United States Patent
Mueller et al.

(10) Patent No.: US 9,939,349 B2
(45) Date of Patent: Apr. 10, 2018

(54) ENDOSCOPY SYSTEM AND CORRESPONDING METHOD FOR EXAMINING GAS TURBINES

(71) Applicant: LUFTHANSA TECHNIK AG, Hamburg (DE)

(72) Inventors: Wolf Mueller, Kaltenkirchen (DE); Michael Thies, Hamburg (DE); Carsten Hoerlyk, Ahrensburg (DE)

(73) Assignee: LUFTHANSA TECHNIK AG, Hamburg (DE)

( * ) Notice: Subject to any disclaimer, the term of this patent is extended or adjusted under 35 U.S.C. 154(b) by 339 days.

(21) Appl. No.: 14/348,223

(22) PCT Filed: Sep. 28, 2012

(86) PCT No.: PCT/EP2012/004089
§ 371 (c)(1),
(2) Date: Jun. 30, 2014

(87) PCT Pub. No.: WO2013/045108
PCT Pub. Date: Apr. 4, 2013

(65) Prior Publication Data
US 2015/0168263 A1    Jun. 18, 2015

(30) Foreign Application Priority Data
Sep. 30, 2011   (DE) .................. 10 2011 114 541

(51) Int. Cl.
*H04N 9/47* (2006.01)
*H04N 7/18* (2006.01)
(Continued)

(52) U.S. Cl.
CPC .......... *G01M 15/14* (2013.01); *F01D 21/003* (2013.01); *G01N 21/8803* (2013.01);
(Continued)

(58) Field of Classification Search
CPC .......... G01M 15/14; G06K 9/00; H04N 5/77; H04N 5/232; G02B 23/24; G01N 21/88
See application file for complete search history.

(56) References Cited

U.S. PATENT DOCUMENTS 5,699,444 A * 12/1997 Palm ..................... G01C 11/06
348/42
5,850,469 A    12/1998 Martin et al.
(Continued)

FOREIGN PATENT DOCUMENTS

| CN | 101354310 A | 1/2009 |
| CN | 101355902 A | 1/2009 |

(Continued)

OTHER PUBLICATIONS

Kim, N.H., S. Pattabhiramanm L.A. Houck III, Bayesian Approach for Fatigue Life Prediction from Field Data, 2010 ASME Turbo Expo Gas Turbine Technical Congress and Exposition, Jun. 14-18, 2010, Glasgow, Scotland, UK.*

*Primary Examiner* — Mohammed Rahaman
*Assistant Examiner* — Richard A Hansell, Jr.
(74) *Attorney, Agent, or Firm* — Saliwanchik, Lloyd & Eisenschenk

(57) ABSTRACT

The invention relates to an endoscopy system and a corresponding method for examining gas turbines, comprising an endoscope and a data processing unit, wherein the endoscope comprises an image recording unit, wherein the endoscope is configured to transmit recorded images of the image recording unit from the inside of the gas turbine to the data processing unit, wherein the endoscopy system is configured to position and align the endoscope comprising the image recording unit introduced into a gas turbine in the gas turbine in a defined manner.

12 Claims, 4 Drawing Sheets

(51) Int. Cl.

| | | |
|---|---|---|
| *G01M 15/14* | (2006.01) | |
| *F01D 21/00* | (2006.01) | |
| *G02B 23/24* | (2006.01) | |
| *G01N 21/954* | (2006.01) | |
| *G01N 21/88* | (2006.01) | |
| *G06K 9/00* | (2006.01) | |
| *H04N 5/232* | (2006.01) | |
| *H04N 5/77* | (2006.01) | |
| *G03B 37/00* | (2006.01) | |

(52) U.S. Cl.
CPC ........... *G01N 21/954* (2013.01); *G02B 23/24* (2013.01); *G02B 23/2407* (2013.01); *G06K 9/00664* (2013.01); *H04N 5/232* (2013.01); *H04N 5/77* (2013.01); *F05D 2260/80* (2013.01); *G01N 2021/9542* (2013.01); *G01N 2201/061* (2013.01); *G01N 2201/12* (2013.01); *G03B 37/005* (2013.01)

(56) References Cited

U.S. PATENT DOCUMENTS

| | | | |
|---|---|---|---|
| 6,009,189 A | 12/1999 | Schaack | |
| 6,063,023 A | 5/2000 | Sakiyama et al. | |
| 6,459,481 B1 | 10/2002 | Schaack | |
| 6,487,909 B2 | 12/2002 | Harrold et al. | |
| 6,652,452 B1 * | 11/2003 | Seifert | A61B 1/00096 600/140 |
| 6,796,709 B2 | 9/2004 | Choi | |
| 7,574,035 B2 * | 8/2009 | Koonankeil | F01D 5/005 348/86 |
| 7,619,728 B2 | 11/2009 | Ogburn et al. | |
| 7,656,445 B2 * | 2/2010 | Heyworth | G01B 11/16 348/265 |
| 8,066,633 B2 | 11/2011 | Itou et al. | |
| 8,322,202 B2 * | 12/2012 | Ehehalt | F01D 17/16 73/112.01 |
| 8,786,848 B2 * | 7/2014 | Hatcher | F01D 9/023 348/83 |
| 2002/0074965 A1 | 6/2002 | Hatley et al. | |
| 2005/0073673 A1 * | 4/2005 | Devitt | F01D 21/003 356/37 |
| 2005/0199832 A1 * | 9/2005 | Twerdochlib | F01D 5/005 250/559.29 |
| 2006/0078193 A1 * | 4/2006 | Brummel | G01N 21/8806 382/152 |
| 2007/0132840 A1 * | 6/2007 | Konomura | G01N 21/954 348/65 |
| 2009/0278924 A1 * | 11/2009 | Heyworth | F01D 21/003 348/82 |
| 2009/0312956 A1 * | 12/2009 | Zombo | F01D 5/288 702/34 |
| 2010/0121141 A1 * | 5/2010 | Rontal | A61B 1/0051 600/106 |
| 2010/0128116 A1 * | 5/2010 | Sato | A61B 1/00045 348/65 |
| 2011/0187707 A1 * | 8/2011 | Kaufman | A61B 1/00009 345/419 |
| 2012/0297600 A1 * | 11/2012 | Ullrich | G01B 11/2441 29/407.04 |

FOREIGN PATENT DOCUMENTS

| | | |
|---|---|---|
| EP | 1408201 A2 | 4/2004 |
| JP | 2005/077832 A | 3/2005 |

* cited by examiner

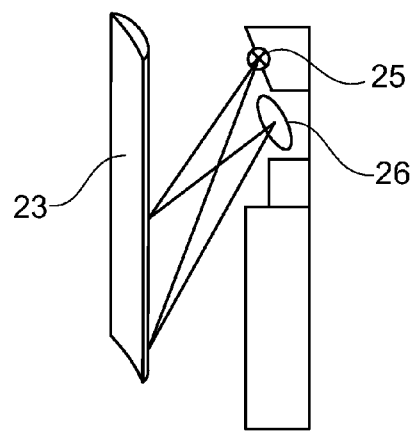
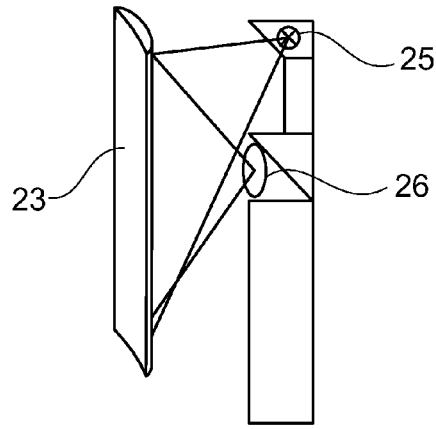
Fig. 4 Fig. 5
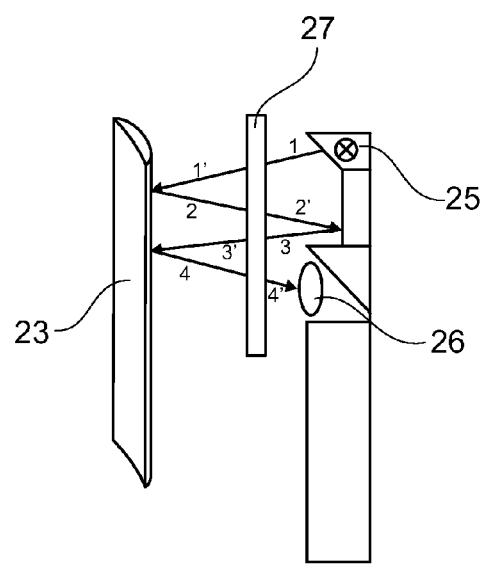
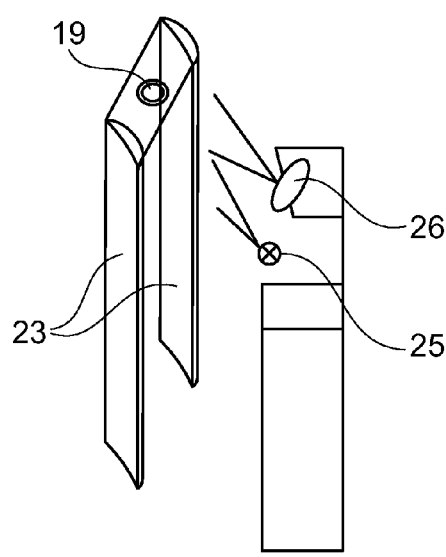
Fig. 6 Fig. 7

ENDOSCOPY SYSTEM AND CORRESPONDING METHOD FOR EXAMINING GAS TURBINES

CROSS REFERENCE TO RELATED PATENT APPLICATIONS

This nonprovisional patent application is filed herewith for the U.S. National Stage under 35 U.S.C. § 371 and claims priority to PCT application PCT/EP2012/004089, with an international filing date of Sep. 28, 2012. The contents of this application are incorporated in their entirety herein.

STATEMENT REGARDING FEDERALLY-SPONSORED RESEARCH OR DEVELOPMENT

Not applicable.

TECHNICAL FIELD

The invention relates to an endoscopy system for examining gas turbines, comprising an endoscope and a data processing device, the endoscope comprising an image recording device, the endoscope being configured to transmit image recordings from the image recording device from inside the gas turbine to the data processing device. In addition, the invention relates to a corresponding method for operating an endoscopy system for examining gas turbines.

BACKGROUND OF THE INVENTION

Endoscopy systems, often referred to as borescope systems, are used for examining gas turbines during maintenance and servicing, and when testing the airworthiness of gas turbines. Known endoscopy systems are controlled by a human operator and are greatly dependent on subjective factors relating to the operator. Known endoscopy systems need long test periods when examining a gas turbine and documenting the results. In the following, the term "endoscope" is used synonymously with the term "borescope".

The problem addressed by the invention is that of providing an endoscopy system and a corresponding method which allow for highly reproducible examination results and short test periods with improved test quality when examining gas turbines.

BRIEF SUMMARY OF THE INVENTION

The invention solves this problem with the features of the independent claims.

According to the invention, the endoscopy system is configured to position and orient the endoscope in a gas turbine in a defined manner, which endoscope has been inserted into the gas turbine and comprises the image recording device.

The defined positioning and orientation by the endoscopy system is particularly advantageous according to the invention because image recordings of particular parts and/or regions inside the gas turbine can be standardized thereby. The image recordings from different examinations of a gas turbine are directly comparable in this way.

Preferably, the endoscopy system comprises an electronically controlled positioning apparatus for positioning and/or orienting the endoscope in the gas turbine in a defined manner. As a result, it is no longer necessary to manually move the endoscope. The positioning and orientation can be controlled by means of the data processing device, so that this positioning can be particularly efficient and rapid.

In addition, the endoscopy system is preferably configured to automatically determine the position and/or orientation of the endoscope in the gas turbine. Checking of the positioning and orientation no longer needs to be performed manually by the operator, and is therefore no longer dependent on subjective factors relating to an operator or to various operators. As a result, the human factor in positioning and orientating the endoscope can be eliminated as a source of errors and imprecision.

The position of the endoscope is preferably determined by image-processing the image recordings using the data processing device. Parts or regions inside the engine are identified in the image recordings by the data processing device, and the position and orientation of the endoscope relative to these parts or regions are determined therefrom. The determined position data can then be used to position and orient the endoscope so that the endoscope can be brought into a position and orientation which are defined according to the invention, and these can be verified. Moreover, other means for determining position can be used in addition or as an alternative.

Preferably, position-defining means are provided between the endoscopy system and the gas turbine. These can include, on the one hand, mechanical means which make it possible for the endoscopy system to be fixed relative to the gas turbine and, on the other hand, mechanical and/or electronic means which make it possible for the coordinate systems of the endoscope and the gas turbine to be synchronized so that the position can be defined. The position-defining means are advantageous for positioning and orienting the endoscope in a defined manner, more particularly for an electronically controlled positioning apparatus. In addition, position-defining means are advantageous for automatically determining the position and/or orientation of the endoscope so that the position and/or orientation of the endoscope can be calibrated.

The endoscopy system is preferably configured to automatically capture images. If the endoscope is in a defined position and orientation, an image-capture of the corresponding parts or regions inside the gas turbine being examined is triggered. It is no longer necessary to manually trigger image-capture, and the length of time taken to examine a gas turbine is therefore reduced.

Preferably, the data processing device is configured to assign image recordings from the image recording device to parts or regions of the gas turbine being examined. In order to assign parts or regions from the inside of a gas turbine to parts or regions which were detected by an image recording, it has to be possible for the corresponding parts or regions to be identified. This can take place on the basis of the defined position and orientation of the endoscope and/or coordinates relating to the gas turbine which are known from the electronically controlled positioning apparatus. Alternatively, the assignment can take place on the basis of image recognition by the data processing device. This is particularly advantageous for documentation which makes it possible to evaluate and review the examination of the gas turbine at a later date.

Preferably, the endoscopy system is configured to automatically store and/or archive image recordings. Produced image recordings are automatically stored and/or archived by the data processing device with the detected parameters, such as date, gas turbine examined and part or region of the gas turbine examined, so that image recordings from an examination of a gas turbine can be electronically deposited in a data set. The storage or archiving is advantageous for evaluating the examination at a later date and for providing evidence of the examination. More particularly, the archiving can be carried out by the data processing device on at least one server allowing for decentralized access to the data set. In addition, parameters for the image-capture, such as illumination, focus and exposure time, are preferably set by the endoscopy system.

Preferably, the image recording device is configured to execute image recordings in accordance with the rotational position of at least one shaft of the gas turbine. The rotational position of a shaft is crucial to the position of rotor blades of a gas turbine. In addition to the defined position and orientation of the endoscope in the gas turbine, the simultaneous defined position and orientation of the endoscope relative to a rotating part or region in a gas turbine is crucial to a corresponding image recording. Defined image details for image recordings of rotating parts or regions of a gas turbine are only produced if the endoscope is in a defined position and orientation and if a particular rotational position of the shaft, to which the rotating part or the rotating region is connected, is set. Therefore, the image recordings are preferably produced in accordance with the rotational position of the corresponding shaft.

In a preferred embodiment, images are captured while the shaft is rotating and in synchronization with the rotational movement of the shaft. In this way, the test speed can be significantly increased and the test duration per gas turbine can be significantly reduced. The synchronization can take place in any suitable manner. Advantageously, the synchronization takes place when a corresponding rotational position is passed which is advantageously defined by a marker, for example the blade lock. The synchronization does not have to take place upon each revolution of the shaft; a synchronization upon every nth revolution of the shaft (n=10, for example) may be sufficient. The rotational position may also be detected by the image recording device. If a stepper motor or synchronous motor were used for driving the shaft, as is also conceivable, the information regarding the angle of rotation or the position is available without additional measurements.

In an alternative embodiment, the rotational position of the shaft is detected by the endoscopy system and is set accordingly for the image-capture.

In a possible embodiment, the endoscopy system is configured to control a rotary apparatus for rotating at least one shaft of the gas turbine. At least one shaft of the gas turbine being examined is connected to a rotary apparatus, which is configured to affect the rotational movement of the shaft. This rotary apparatus can be controlled by the endoscopy system so that the rotational position of the shaft and thus the image details for the image recordings can be set. In a preferred embodiment, the rotary apparatus is configured to produce a rotation or a continuous adjustment of the rotational position of at least one shaft, more particularly to make it possible to capture images in synchronization with the rotation of the shaft. Alternatively, the rotation can be carried out manually.

The data processing device is preferably configured to compare image recordings with reference image recordings and/or with archived image recordings. The defined positioning and orientation according to the invention of the endoscope by the endoscopy system is particularly advantageous for a comparison of image recordings of parts or regions of a gas turbine, since it makes it possible for a plurality of image recordings to be advantageously compared using image processing means. A comparison of a plurality of image recordings is advantageous for being able to automatically identify differences in parts or regions of a gas turbine among a plurality of examinations, and for marking the identified differences in a suitable manner.

Preferably, the data processing device is configured to automatically identify deviations from the desired state and/or damage to parts or regions of the gas turbine being examined. The deviation from the desired state can be determined by a comparison with a reference recording. An archived image recording which shows, for example, the gas turbine in the new or as-new condition can be considered to be a reference image. Alternatively, a reference recording can come from another gas turbine. In addition, a computer-generated image can be used as a reference recording. Automatically identifying deviations from the desired state and/or damage is particularly advantageous for examining a gas turbine because, for example, damage identified by the endoscopy system can be brought to the attention of the operator during evaluation. As a result, the error probability when identifying damage can be further reduced by the operator. In addition, it is possible for only image recordings containing identified deviations and damage to be presented to the operator for assessment. This reduces the operator's workload and the test time required.

Preferably, the data processing device is configured to gauge damage to parts or regions inside a gas turbine. The geometric dimensions of damage to a gas turbine, such as cracks or dents, are of crucial significance to the assessment of the damage. The damage is gauged with reference to image recordings by the data processing system. This gauging can be aided by known dimensions of parts in the image recording and/or by the defined position and orientation of the endoscope relative to the parts or regions in the image recording and the dimensions, which can be generated therefrom, of parts or regions in an image recording. This is advantageous because damage is generally assessed on the basis of the geometric dimensions thereof.

Preferably, the data processing device is configured to classify damage to parts or regions inside a gas turbine. Classification can be carried out for example on the basis of the extent of deviations from the desired state and/or on the basis of the extent of damage. In addition, it is possible for classification to also be carried out according to the type of parts or regions, so that relatively small amounts of damage to critical parts are classified differently from that to non-critical parts. Alternatively, classification can be made according to the type of damage or to the deviation. In addition, classification of the damage can be made according to its influence on the airworthiness of a gas turbine used in an aircraft, for example according to damage which only needs to be repaired at the next overhaul or according to damage which impairs airworthiness. Combinations of these classifications are also possible. Classification is preferably used to reduce the test time and to simplify the documentation. For example, when examining using the endoscopy system according to the invention, damage classified as critical can be presented to an operator first so that, in the event of a shutdown possibly being necessary, these findings can be identified at an early stage of the examination.

Preferably, the data processing device is configured to track the progression of damage to parts or regions inside a gas turbine. Detected damage is compared with archived image recordings by the data processing device. The progression of the extent of damage, such as cracks, can be tracked over time on the basis of archived image recordings of earlier examinations. This can be carried out either using an image or on the basis of geometric dimensions. As a result, it can be identified whether or not a defect has become larger or, for example the size of a crack, has remained stable between different examinations of a gas turbine.

Preferably, the data processing device is configured to carry out a forecasting procedure in order to forecast the further progression of damage to parts or regions inside the gas turbine being examined. If the values relating to the damage, such as the length of a crack, are known for a plurality of times at which an engine was examined, values relating to the damage, such as the rate of progression of a crack, can be determined by means of the operating profiles of the turbine being examined and of a damage model implemented in the data processing device. A forecast of the further expected progression of damage can be produced therefrom by the data processing device. This is advantageous for efficient scheduling of overhaul or repair of the gas turbine and for operational safety.

In addition, a method for examining gas turbines using an endoscopy system according to the invention is provided in which, in a first method step, the endoscope of the endoscopy system according to the invention is inserted into the inside of a gas turbine. In the next method step, the endoscope of the endoscopy system is positioned and oriented in a defined manner inside the gas turbine by the data processing device. In the final method step, image recordings of parts or regions of the gas turbine are produced from the defined position and orientation by the image recording device.

BRIEF DESCRIPTION OF THE SEVERAL VIEWS OF THE DRAWINGS

The invention is explained in the following on the basis of preferred embodiments with reference to the accompanying drawings, in which:

FIGS. 4 to 7 are schematic views of various image-recording and/or illumination geometries.

DETAILED DESCRIPTION OF THE INVENTION

Figure 1:
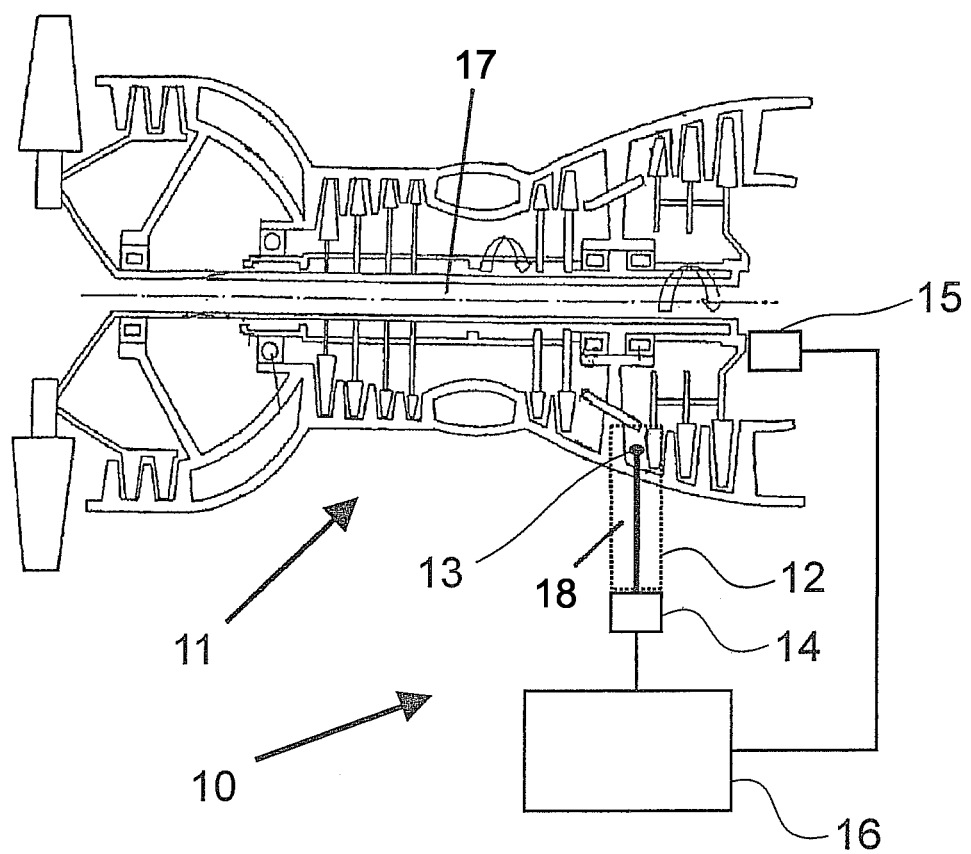
FIG. 1 is a schematic view of an examination of a gas turbine using the endoscopy system.

FIG. 1 schematically shows the endoscopy system 10 according to the invention during examination of a gas turbine 11. The endoscope 12 of the endoscopy system 10 preferably comprises a shank 18 for inserting the endoscope 12 into the gas turbine 11 and an image recording device 13 which can produce image recordings 20, 21, 22 of the inside of the gas turbine 11 (see FIG. 2). The image recording device 13, which is preferably arranged at a free end of the shank 18, may preferably be a camera and typically comprises a lens and a camera chip or image sensor for detecting images and conversion into electronic image data. It is possible for parts of the camera 13, for example the image sensor, to be arranged so as to be remote from the camera lens arranged at the free end of the shank 18, in particular for space reasons. In this case, the image information can for example be guided from the camera lens to the image sensor by means of an optical wave guide extending through the shank. In one embodiment, the image recording device 13 may for example be a Scheimpflug camera; however, the invention is in no way limited to this type of camera.

In a further embodiment, a plurality of cameras can be used, for example a color-recognition camera and a rapid black/white-recognition camera. In addition, a plurality of endoscopes which each comprise a camera can, for example, be provided. Alternatively, an endoscope can be provided in which the image recording device 13 comprises a plurality of cameras. The camera for the final series of recordings can for example be selected on the basis of the recording situation.

A positioning apparatus 14 is connected to the endoscope 12 and configured to position the endoscope 12 inside the gas turbine 11. Preferably, a rotary apparatus 15 or a rotary drive is provided for rotating the shaft 17 of the gas turbine 11.

A data processing device 16 is provided for controlling the endoscopy system 10 and for processing the data gathered by the endoscope 12. In order to compensate distortions in scale and achieve standardization, the image processing preferably includes rectification of the recorded images.

In a typical examination of a gas turbine 11, the endoscope 12 is initially inserted into the portion of the gas turbine 11 to be examined. For this purpose, the endoscope 12 is inserted through a suitable opening in the gas turbine 11.

In an advantageous embodiment, when inserting the endoscope 12 into a gas turbine 11, position-defining means are used. These can be a mechanical stop or a mechanical connection which makes it possible for there to be a predetermined link between the coordinate systems of the endoscope system 10 and of the gas turbine 11, so that the relative position of the endoscope 12 and the gas turbine 11 is defined by position-defining means. In a further possible embodiment, the position-defining means are in the form of measuring technology which makes it possible to compare the relative position.

The position of the endoscope 12, more particularly of the image recording device 13, inside the gas turbine 11 can be automatically determined on the one hand on the basis of the position-defining means, preferably using a subsequent measurement of the further movements of the endoscope 12. Alternatively or additionally, the position can be automatically determined on the basis of the image information which is transmitted to the data processing device 16 by the image recording device 13. Determining the position from data from the image recording device 13 is particularly advantageous for precision positioning, since exact adherence to the position and orientation of the image recording device 13 in the gas turbine 11 can be directly checked in this way.

Preferably, the rotational position or the angle of rotation of the shaft 17 is automatically determined. In a possible embodiment, this can be carried out by the image recording device 13 and suitable image processing in the data processing device 16. The absolute rotational position of the shaft 17 can in particular be determined on the basis of a marker or a suitable reference point. Advantageously, the blade lock 19, which is generally already present, is detected as a marker or reference point for each image processing procedure. Alternatively or additionally, one or more additional markers can be provided. The position of individual turbine blades 23 can be determined relative to the marker, so that the identity of the individual turbine blades 23 is known.

In alternative embodiments, an additional sensor can be provided for detecting the rotational position of rotating parts of the gas turbine 11.

The endoscope 12 is moved by an electronically controlled positioning apparatus 14, which can be operated by manual input and/or can be automatically controlled by the data processing apparatus 16. The positioning apparatus 14 assumes the positioning and orientation of the image recording device 13 of the endoscope 12 relative to the gas turbine 11. This is carried out by electronically controlled actuators, which make it possible to precisely move the endoscope 12. In a possible embodiment, the actuators are equipped with corresponding sensor technology to allow a measurement of the travel distance to be provided to the data processing device 16. The measurement of the travel distance of the actuators of the positioning apparatus 14 can also be the basis for automatically determining a position. The positioning apparatus can be connected to the endoscope at the end thereof that is not inserted into a gas turbine. In addition, the endoscope can include the positioning apparatus or parts thereof.

In addition, for capturing images, in a defined manner, of rotating parts of the gas turbine 11, knowledge of a defined relationship between the rotational positions relative to the endoscope 12 is advantageous. For this purpose, an electronically controlled rotary apparatus 15, which can rotate at least one shaft of the gas turbine 11 being examined, is controlled by the data processing device 16. In a possible embodiment, the rotary apparatus 15 can be used to produce continuous rotation of at least one shaft.

In an advantageous embodiment, the images are captured by the image recording device 13 when the shaft is continuously rotating. The image recording device is then preferably configured to capture images in synchronization with the rotational movement of the shaft 17 of the gas turbine 11. The synchronization can advantageously be carried out on the basis of a marker of the rotational position of the shaft 17, for example of the blade lock 19. Alternatively or additionally, image-capture can be triggered at a measured position of one or more turbine blades 23.

In a practical method sequence, a test run can be carried out first in which, for example, the instantaneous speed of the turbine blades 23 is determined or estimated. From the test run, rate times are for example determined which can then be used for carrying out the final series of recordings.

In an alternative embodiment, the rotary apparatus 15 specifically sets one or more rotational positions of the shaft 17 and maintains the set position, in particular as the images are being captured.

The defined positioning and orientation of the endoscope 12 using the endoscopy system 10 according to the invention allows for standardized image recordings 20, 21, 22 (see FIG. 2) of parts or regions inside the gas turbine 11.

Parts and regions inside the gas turbine 11 are preferably all objects which have a surface which is impinged upon by the gas flow of the gas turbine 11, in particular rotor and stator blades, linings and combustion chambers. In addition, these are all regions of a gas turbine 11 which, when assembled, are accessible for examination or testing by specific access using endoscopy. A particular part in a gas turbine 11 may for example be rotor blade number 3 in the first stage of the high-pressure turbine. The defined positioning and orientation of the endoscope 12 in the gas turbine 11 and the corresponding rotational position allow for the defined image-capture of this part from a particular direction, so that the image recording 20, 21, 22 shows this part together with a particular region of its surface.

For a targeted examination and the documentation thereof, it is advantageous to assign an image recording 20, 21, 22 to a part of the gas turbine 11 being examined. In a preferred embodiment, the endoscopy system 10 is therefore configured to automatically assign parts to image recordings 20, 21, 22. This can take place for example on the basis of position data and/or by automatic image recognition by the data processing device 16 of at least one marker or sign which is suitable for determining the identity of parts. A suitable marker is for example a blade lock 19, which can represent an unambiguous zero position for the blades, whereby it is possible to unambiguously assign the blades by simply counting starting from this zero position.

In addition to the relative position and orientation of the image recording device 13 with respect to the recorded object, the settings of the image recording device 13 are also crucial to the standardized capture of images. Therefore, in a preferred embodiment, the settings of the image recording device 13 are controlled by the data processing device 16. These settings can be focus, shutter speed, cropping and illumination by a light source, for example.

In embodiments of the invention, a light source 25 is provided to actively illuminate the surface to be recorded. Various geometries and arrangements of the light source 25 relative to the lens 26 and the corresponding aperture are shown in FIGS. 4 to 7. In order to prevent interference in the images owing to the direct reflection of the light beam of the light source 25 on the surface to be recorded, obliquely incident illumination can for example be provided, as shown for example in FIGS. 4, 5 and 7, the arrangement being selected such that no light beam from the light source 25 is directly reflected on the lens 26.

It is also possible to use a filter 27 (see FIG. 6), for example a Fourier filter utilizing the dark field effect, or a density filter. In addition, regular radiometric calibration of the image recording device 13 may be advantageous.

In a preferred embodiment, the endoscopy system 10 is capable of carrying out automatic image-capture. The image recording device 13 typically continuously supplies image data to the data processing device 16, which data can be evaluated for the purposes of image recognition, position recognition, rotational position recognition and recognition of parts and/or regions. The actual image-capture produces an image recording 20, 21, 22 which is suitable for the purposes of examining the gas turbine 11. Therefore, the image recording 20, 21, 22 includes the appropriate portion of a part, for example of a turbine blade 23. If the data processing device 16, using appropriate means, identifies that the image data, position data and preferably also the assignment match the defined target values, then automatic image-capture follows. The corresponding data are associated with the image recording 20, 21, 22 by the data processing device. Since images are captured automatically, it is not necessary to manually control the relevant parameters, and the operator of the gas turbine 11 can be directly provided by the endoscopy system 10 with an image recording 20, 21, 22 that is suitable for further evaluation.

In a preferred embodiment, the image recordings 20, 21, 22 are automatically stored and archived so that they are available at a later date for documentation, evaluation and evidence. The archiving can take place directly in the data processing device 16 of the endoscopy system 10 or in a central database, so that a plurality of endoscopy systems 10 can access the same database.

In addition, in a possible embodiment, the endoscopy system 10 according to the invention is equipped with an image recording device 13 which is a stereo recording device.

In a further possible embodiment, the endoscope 12 comprises at least one diagnostic device for examining parts or regions inside a gas turbine 11 in a non-destructive manner. The additional diagnostic device may include various options for non-destructive testing, such as an eddy current probe or a diagnostic device for dye penetrant testing.

The field of application for the endoscopy system 10 according to the invention when examining gas turbines 11 includes the examination of jet engines of aircraft, such as turbofans or turbojets and/or jet engines used in industry, such as marine turbines or turbines in power-generating systems.

Figure 2:
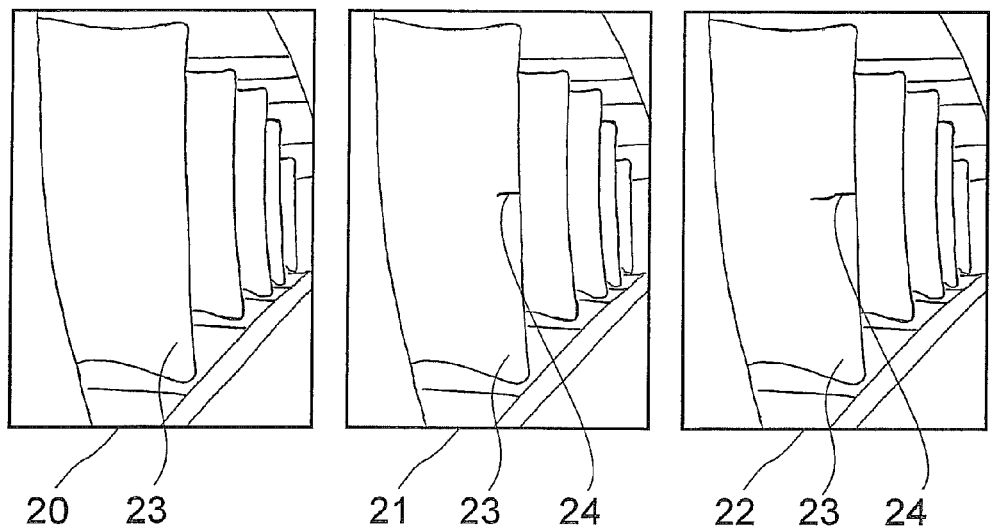
FIG. 2 shows a plurality of image recordings of examinations of a region of a gas turbine using the endoscopy system.
Figure 3:
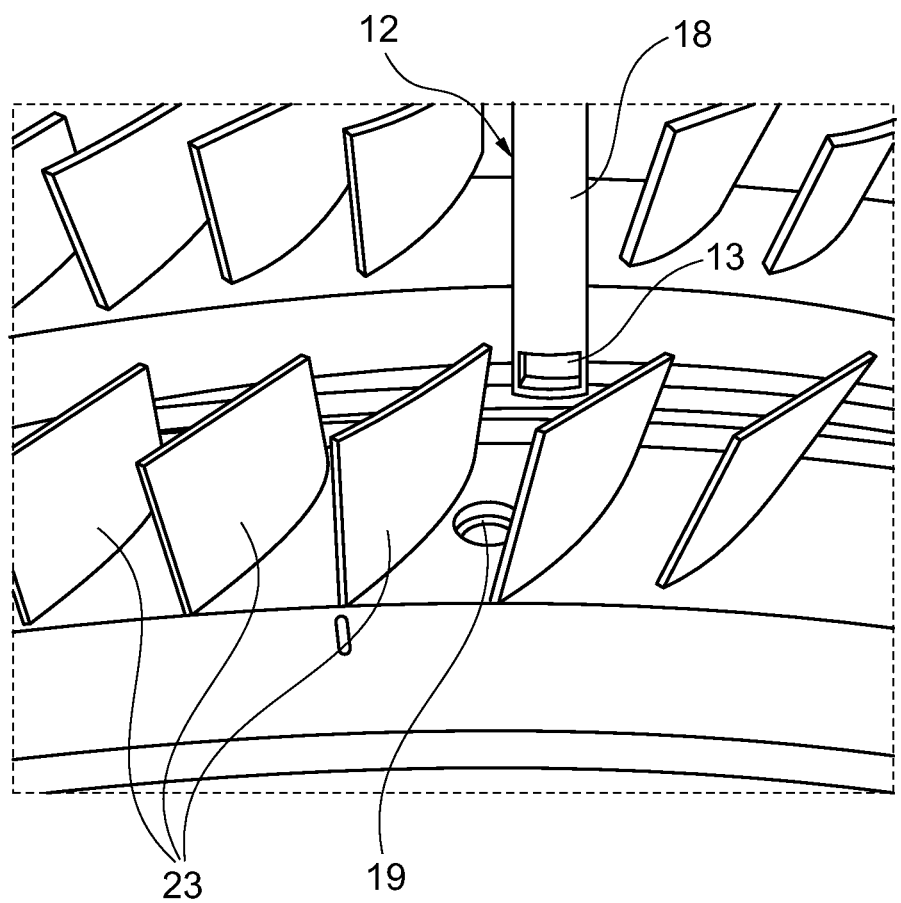
FIG. 3 is a perspective view of an endoscope and of a blade wheel to be examined in a gas turbine.

FIG. 2 shows a plurality of image recordings 20, 21, 22 of examinations of a region of gas turbine 11 using the endoscopy system 10 according to the invention, which image recordings each show the same image detail from the inside of a gas turbine 11. Rotor blades of a high-pressure turbine stage are shown, each of the rear edges of the rotor blades in the image detail being hidden by the blade in front. In this embodiment, the turbine blade 23 to be examined is shown in the foreground.

Image recording 20 shows the turbine blade 23 in its reference state. The image recording 20 of the reference state is used to show the optimum technical state of the turbine blade 23 and either can be an archived image recording 20 of the gas turbine 11 in this state or can be generated specifically for this purpose as a reference. This reference image recording 20 can be stored in the data processing device 16 or in the central database. The information regarding position and orientation of the image recording device 13, by means of which the image recording 20 was produced, is associated with the image recording 20 and, according to the invention, the position and orientation of the endoscope 12 and image recording device 13 are used in all further image recordings 21 and 22 of subsequent examinations of the turbine blade 23, by means of which the position and orientation of the endoscope 12 is defined.

In image recordings 20, 21, 22, the embodiment shows the corresponding turbine blade 23 of the gas turbine 11 in different examinations, so that the gas turbine 11 has a particular operating time between examinations. Image recording 22 shows the turbine blade 23 with the longest operating time, compared with image recording 20 with the shortest operating time of the three image recordings 20, 21 and 22. A number of operating hours can thus be assigned to the image recordings 20, 21, 22.

The advantage according to the invention of defined positioning and orientation of the endoscope 12 can be seen with reference to the image recordings 20, 21 and 22. The same positioning and orientation in different examinations results in very good comparability of the various image recordings 20, 21, 22. On the one hand this is advantageous for manual review by the operator, and on the other hand it makes it possible for differences and changes to be easily identified during electronic processing. For example, by superposing image recordings 20 and 21, the crack 24 can be very easily identified. Since the image recording 20 is used in this embodiment as a reference image, the crack 24 can be very rapidly identified as a deviation from the desired state.

In a preferred embodiment, the data processing device 16 automatically identifies this deviation from the desired state and for example adds a corresponding indicator into the image recording 21 for review by the operator. Further possible deviations from the desired state that can be identified by the endoscopy system 10 according to the invention in this embodiment are damage such as wear, cracks, dents, holes or foreign objects.

In one embodiment, the data processing device 16 of the endoscopy system 10 is configured to gauge damage. The crack 24 is gauged for example with reference to the image data and corresponding references, and the data processing device 16 outputs a corresponding geometric crack length.

In a further advantageous embodiment, the endoscopy system 10 can automatically classify the damage, for example the crack 24 is initially classified as a crack by the data processing device 16. Further classification can take place for example with reference to the crack length, which in this embodiment is within accepted limits and thus will not impair operational safety until the next planned examination of the gas turbine 11. The classification can be provided to the operator, who can search for certain types of damage in a targeted manner. If the data processing device 16 identifies fatal damage, for example, this can be accordingly clearly marked for the operator in the documentation and in the image.

Image recording 22 shows the same turbine blade 23 in a later examination. The comparison of image recording 22 with the image recordings 20 and 21 shows a deviation from the desired state shown in image recording 20 and a change in the damage found in the previous examination, image recording 21. The crack 24 has thus continued to grow during the intervening period of operation of the gas turbine. In this embodiment, the data processing device 16 is configured to automatically identify and gauge the crack 24 and to assign a number of operating hours to the gas turbine 11 and/or the turbine blade 23. It is thus possible to track the crack 24 over time in terms of operating hours, by means of which it can be seen that the crack 24 has continued to grow. In addition, the point in time at which the damage occurred can thus be narrowed down. In this example, the damage would have occurred between image recordings 20 and 21.

In a preferred embodiment, the information regarding the progression of the damage is used in the data processing device 16 to forecast the further progression of the damage in the future. As a result, the point in time at which a critical crack length occurred can be more precisely estimated, and the maintenance intervals can be adapted accordingly. In a further possible embodiment, the data processing device 16 is configured to optimize the forecasting procedure for forecasting the progression of damage on the basis of archived image recordings 20, 21, 22 of a large number of gas turbines 11.

What is claimed is:

1. An endoscopy system for examining a gas turbine, comprising:
   an endoscope;
   a data processing device,
   wherein the endoscope comprises:
      an image recording device,
   wherein the endoscope is configured to be inserted into a gas turbine, capture one or more image recordings of an inside of the gas turbine via the image recording device, and transmit the one or more image recordings of the inside of the gas turbine from the image recording device to the data processing device,
   wherein the data processing device is configured to process the one or more image recordings of the inside of the gas turbine so as to determine a position and orientation of the endoscope in the gas turbine, wherein the data processing device is configured to process the one or more image recordings of the inside of the gas turbine so as to automatically determine a rotational position or an angle of rotation of a first shaft of the at least one shaft based on a marker or reference point in the one or more image recordings of the inside of the gas turbine, and wherein the marker or reference point is a blade lock of the gas turbine, wherein the data processing device is configured to assign image recordings of the inside of the gas turbine of the one or more image recordings of the inside of the gas turbine to parts or regions of the gas turbine by automatic image recognition of the marker or reference point; and an electronically-controlled positioning apparatus, wherein the electronically-controlled positioning apparatus is configured to position and orient the endoscope in the gas turbine, wherein the endoscopy system is configured to use the position and orientation of the endoscope in the gas turbine determined via the data processing device to position and orient the endoscope in the gas turbine in a defined position and orientation of the endoscope in the gas turbine via the electronically-controlled positioning apparatus, and wherein the endoscopy system is configured to control a rotary apparatus for rotating at least one shaft of the gas turbine.

2. The endoscopy system according to claim 1,
wherein the endoscopy system is configured to determine a relative position of the endoscope and the gas turbine.

3. The endoscopy system according to claim 1,
wherein the endoscopy system is configured to automatically capture image recordings of the inside of the gas turbine.

4. The endoscopy system according to claim 1,
wherein the endoscopy system is configured to automatically store or archive image recordings of the inside of the gas turbine.

5. The endoscopy system according to claim 1,
wherein the endoscopy system is configured to capture at least one image recording at a corresponding at least one rotational position of the at least one shaft of the gas turbine.

6. The endoscopy system according to claim 1,
wherein the image recording device is configured to capture image recordings in synchronization with a rotational movement of the at least one shaft of the gas turbine.

7. The endoscopy system according to claim 1,
wherein the data processing device is configured to compare image recordings of the inside of the gas turbine with reference image recordings of the inside of the gas turbine and/or with archived image recordings of the inside of the gas turbine.

8. The endoscopy system according to claim 1,
wherein the data processing device is configured to automatically identify deviations from a desired state and/or damage to parts or regions of the gas turbine.

9. The endoscopy system according to claim 1,
wherein the data processing device is configured to gauge and/or classify and/or track progression of damage to parts or regions inside the gas turbine.

10. The endoscopy system according to claim 1,
wherein the data processing device is configured to carry out a forecasting procedure in order to forecast further progression of damage to parts or regions inside the gas turbine.

11. A method for examining a gas turbine using an endoscopy system according to claim 1, comprising:
inserting the endoscope of the endoscopy system into a gas turbine;
capturing one or more image recordings of an inside of the gas turbine via the image recording device;
transmitting the one or more image recordings of the inside of the gas turbine from the image recording device to the data processing device;
processing the one or more image recordings of the inside of the gas turbine so as to determine a position and orientation of the endoscope in the gas turbine via the data processing device;
positioning and orienting the endoscope in the gas turbine in the defined position and orientation of the endoscope in the gas turbine determined via the data processing device, via the electronically-controlled positioning apparatus; and
producing image recordings of parts or regions of the gas turbine via the image recording device.

12. The endoscopy system according to claim 2,
wherein the endoscopy system is configured to use:
the position and orientation of the endoscope in the gas turbine determined via the data processing device; and
the relative position of the endoscope and the gas turbine,
to position and orient the endoscope in the gas turbine in the defined position and orientation of the endoscope in the gas turbine via the electronically-controlled positioning apparatus.

* * * * *